United States Patent [19]

Janssen

[11] Patent Number: 5,454,809
[45] Date of Patent: Oct. 3, 1995

[54] ELECTROSURGICAL CATHETER AND METHOD FOR RESOLVING ATHEROSCLEROTIC PLAQUE BY RADIO FREQUENCY SPARKING

[75] Inventor: Michael Janssen, Englewood, Colo.

[73] Assignee: Angioplasty Systems, Inc., Englewood, Colo.

[21] Appl. No.: 230,439

[22] Filed: Apr. 19, 1994

Related U.S. Application Data

[63] Continuation of Ser. No. 96,651, Jul. 22, 1993, abandoned, which is a continuation of Ser. No. 974,670, Nov. 22, 1992, abandoned, which is a continuation of Ser. No. 849,638, Mar. 5, 1992, abandoned, which is a continuation of Ser. No. 637,992, Jan. 3, 1991, abandoned, which is a continuation of Ser. No. 294,270, Jan. 6, 1989, abandoned.

[51] Int. Cl.$^6$ ............................................. A61B 17/39
[52] U.S. Cl. ........................... 606/41; 606/48; 606/50; 128/660.03
[58] Field of Search .................... 128/660.03; 607/122; 606/33, 34, 41, 42, 46, 48, 50

[56] References Cited

U.S. PATENT DOCUMENTS

| | | | |
|---|---|---|---|
| 4,532,924 | 8/1985 | Auth et al. | 606/50 |
| 4,576,177 | 3/1986 | Webster, Jr. | 128/660.03 |
| 4,643,186 | 2/1987 | Rosen et al. | 606/33 |
| 4,682,596 | 7/1987 | Bales et al. | 606/41 |

FOREIGN PATENT DOCUMENTS 3516830  11/1986  Germany .................. 128/786

OTHER PUBLICATIONS

Slager et al, "Vaporization . . . Erosion", JACC, Jun. 1985, pp. 1382–1386.

Primary Examiner—Lee S. Cohen
Attorney, Agent, or Firm—Beaton & Folsom

[57] ABSTRACT

A method, and device utilized to practice it, for the resolution of tissue by radio frequency sparking. The device of the present invention having a distal end which is insertable within and along the lumen of a tubular body member and manipulated there through to desired position where the device will be operated. The device comprises an elongated flexible hollow tube having a distal end, a proximal end, and a diameter smaller than the diameter of the tubular, body member into which the device is being inserted; passage means within the tube; a plurality of electrodes adjacent the distal end of the device; and means for selectively supplying radio frequency electrical current to at least one of said electrodes.

18 Claims, 2 Drawing Sheets

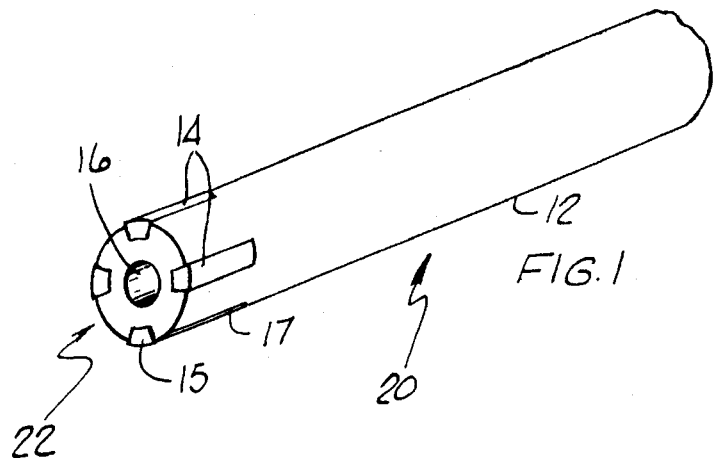
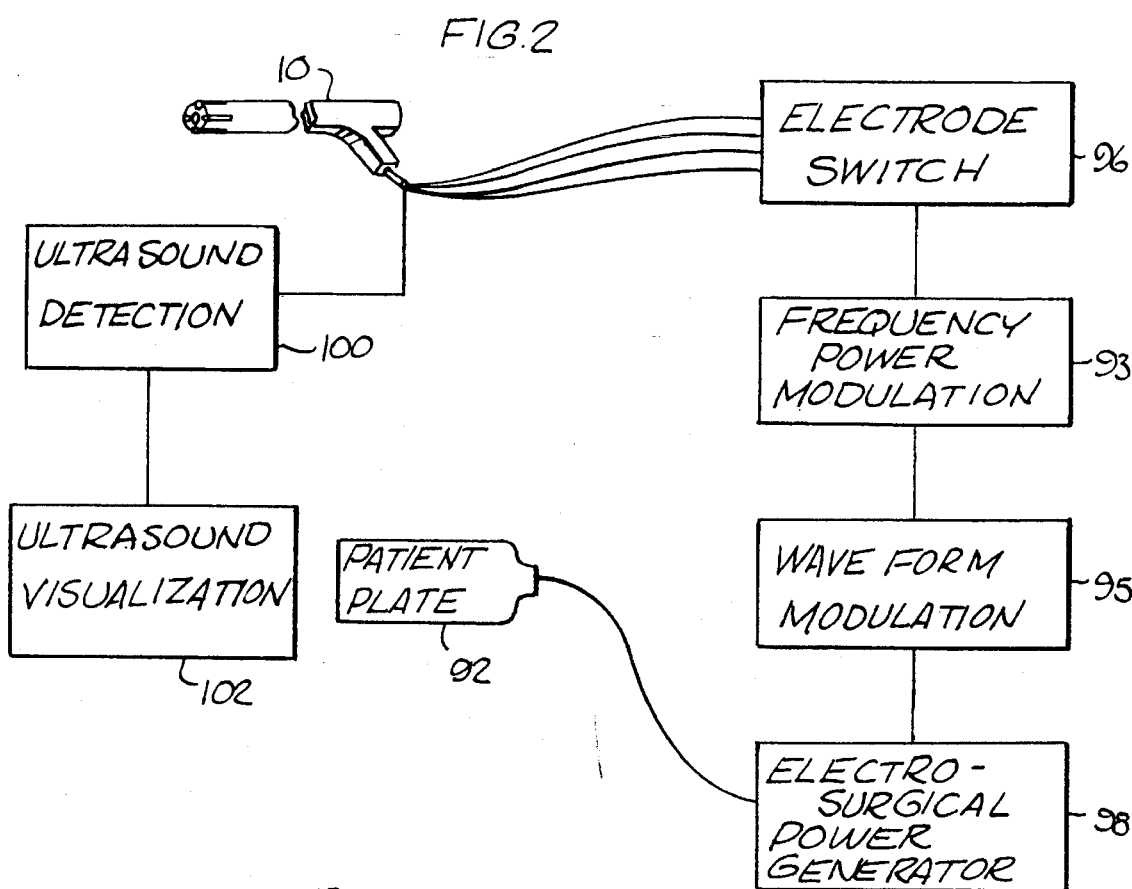
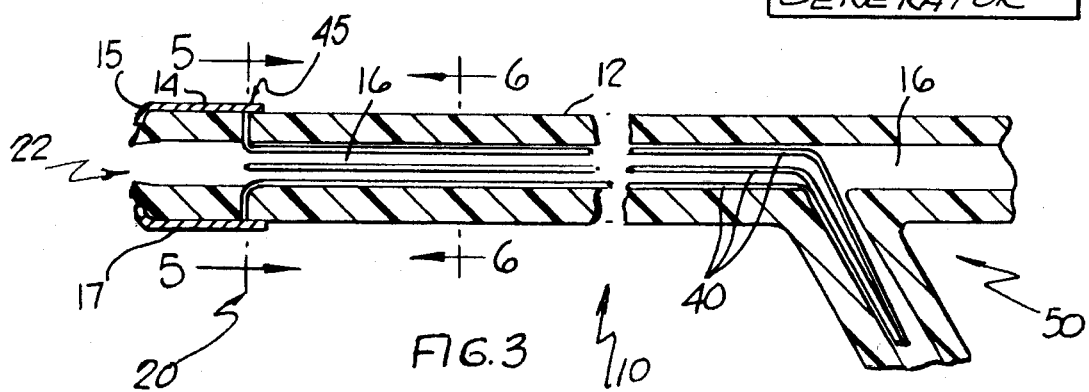

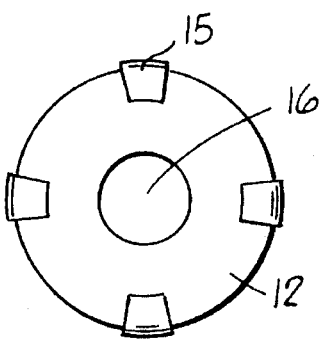
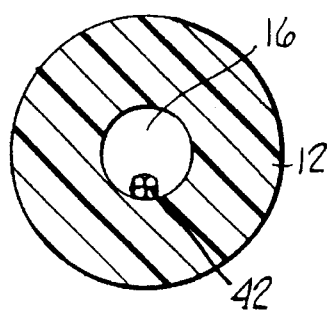
FIG.4
FIG.9
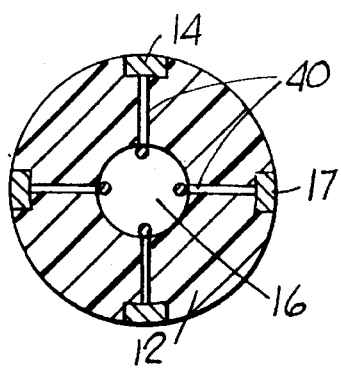
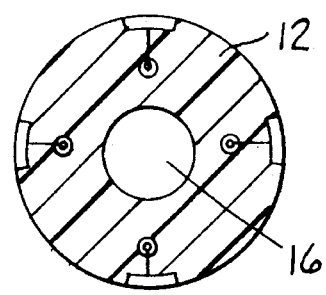
FIG.5
FIG.10
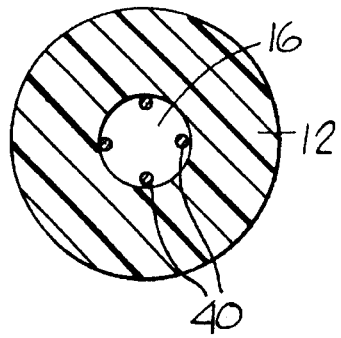
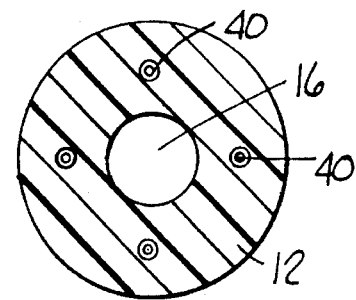
FIG.6
FIG.11
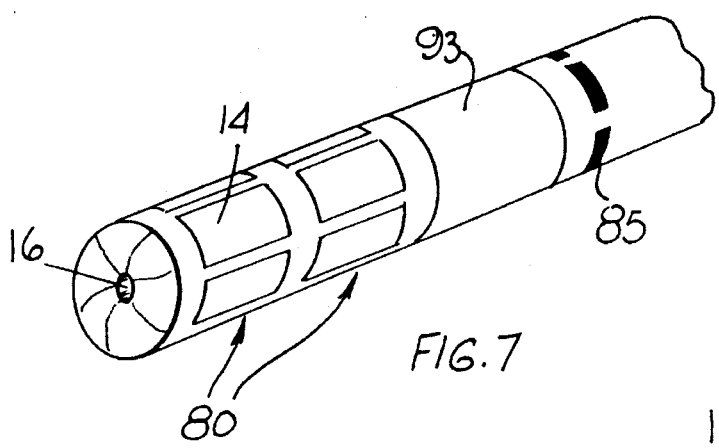
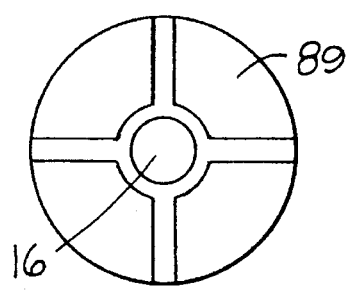
FIG.7
FIG.8

ELECTROSURGICAL CATHETER AND METHOD FOR RESOLVING ATHEROSCLEROTIC PLAQUE BY RADIO FREQUENCY SPARKING

This is a continuation of application Ser. No. 08/096,651 filed Jul. 22, 1993, now abandoned, which is a continuation of Ser. No. 07/974,670 filed on Nov. 22, 1992, now abandoned, which is a continuation of Ser. No. 07/849,638 filed Mar. 5, 1992, now abandoned, which is a continuation of Ser. No. 07/637,992 filed Jan. 3, 1991, now abandoned, which is a continuation of Ser. No. 07/294,270 filed Jan. 6, 1989, now abandoned.

FIELD OF THE INVENTION

The present invention relates to a device and method for resolving or removing atherosclerotic plaque build-up in an artery in order to improve blood flow. The device consists of an electrosurgical catheter which has a plurality of electrode sites, each capable of resolving plaque via radio frequency ("RF") sparking between the electrodes and the plaque. The current generated at the selected electrode is modulated so that the fatty material of the plaque is resolved without creating significant amounts of residue.

BACKGROUND OF THE INVENTION

Various angioplasty techniques have been in use for several years. Typically, a catheter is introduced into the body through an artery in the leg or arm and threaded into the artery or blood vessel that has restricted blood flow due to the build-up of atherosclerotic plaque. The most common technique in current practice is balloon angioplasty. The catheter positioned within the subject artery has a deflated balloon at its tip. The balloon is inflated within the artery and the expansion of the balloon is designed to "press" the plaque into the artery wall, thereby minimizing blood flow restrictions. Balloon angioplasty generally just manipulates the form of the plaque, and does not create a significant problem of plaque residue flowing from the site. Unfortunately, balloon angioplasty has several failings and a relatively high complication rate.

Atherosclerotic plaque build-up can exist in a number of different forms. The plaque can be quite hard and scaly or more fatty and pliable. The areas of plaque accumulation are generally not symmetrically located at a particular point in the artery, rather adhering to only portions of the artery walls.

Considerable efforts have been directed toward finding improved means to perform angioplasty procedures. Numerous devices recently have been described that utilize the application of heat to resolve atherosclerotic plaque. See for example, U.S. Pat. Nos. 4,654,024 of Crittendon et al. and 4,748,979 and 4,672,962 of Hershenson. The most extensive research concerning the use of heat to resolve atherosclerotic plaque has been directed toward the area of laser angioplasty techniques. In most laser angioplasty devices the laser is used simply to supply heat to the tip of the catheter. See for example, U.S. Pat. Nos. 4,784,133 of Mackin; 4,685,458 of Lechrone; 4,770,653 of Shturman; 4,662,368 and 4,773,413 of Hussein; and 4,732,448 and 4,641,912 of Goldenberg.

The various angioplasty techniques described in the literature uniformly fail to address the asymmetric disposition of the plaque within the artery. In most cases, the tip of the angioplasty catheter acts as if the plaque consists of a uniform symmetric coating on the interior wall of the artery. Particularly in those techniques which use something other than pressure to manipulate the plaque, the resolving forces are applied indiscriminately to the plaque and to the healthy tissue within the artery.

Radio frequency sparking to cut or cauterize tissue as a medical procedure is common in the prior art. There are two basic classes of electrosurgical devices. Monopolar devices consist of a high-frequency electrical (generally RF) generator, a cutting or cauterizing electrode or needle, and a patient plate. The patient plate is attached to the body of the patient, and acts as the return electrode for completion of the RF circuit. Cutting occurs due to the heat generated by RF sparking from the electrode to the patient's body tissue. The shape of the electrode concentrates the RF energy, thus creating the high temperature spark. Appropriate modulation of the frequency determines whether cutting or cauterizing will occur. The relatively larger surface area of the patient plate, which is in contact with the patient's body, prevents the current flow from concentrating at one point. This prevents the RF current from burning the patient as the current exits the body.

There are also several bipolar electrosurgical devices described in the prior art. Bipolar devices consist of a high frequency electrical generator and an instrument that contains both the delivery and return electrode. RF sparking occurs between the two self-contained electrodes of the instrument. The bipolar electrosurgical devices of the prior art are generally inadequate due to the conditions necessary to create bipolar sparking. The most fundamental difficulty is that bioactive electrodes must have a roughly equal voltage drop at both the delivery and return electrodes. The high power current required in order to achieve bipolar arcing often causes extraneous sparking-particularly when there is unequal contact with the surrounding tissue.

The extension of known electrosurgical processes—utilizing RF sparking—to angioplasty techniques is relatively unexplored. A disclosure of a monopolar electrosurgical catheter for use in resolving atherosclerotic plaque is found in U.S. Pat. No. 4,682,596 of Bales. The mono and bipolar devices in Bales describe a hollow catheter with a hollow tip member. Only one potential electrode, at the catheter tip, is envisioned by the Bales patent. Bales briefly describes the utilization of variously modulated waveforms in order to resolve atherosclerotic plaque, and the application of high power levels while minimizing the creation of excessive amounts of heat. However, means are included for removing residue from the plaque destruction site, indicating that the modulation techniques employed have not been maximized. It should be possible to destroy the plaque in such a manner so as to eliminate significant residue formation.

An article by Cornelius J. Slager et al. in the *Journal of the American College of Cardiology* entitled "Vaporization of Atherosclerotic Plaque by Spark Erosion" (Jun. 1985, pp. 1382-6) describes the use of a bipolar RF sparking catheter. Again, there is a single spark generating electrode. The sparking frequency is modulated, but not to optimize ablation. Synchronous transmission of energy with cardiac contraction is employed in order to minimize the disruption of electrical pathways in the heart.

U.S. Pat. No. 4,643,186 of Rosen describes an "antenna" type bipolar RF sparking catheter for use in angioplasty. The delivery and return electrodes are configured in such a way that the electrodes terminate together to form an "antenna."

When current is supplied to the antenna, RF sparking will occur. The addition of balloon means encapsulating the sparking antenna is also described. Rosen discloses coating the interior surface of such balloons in order to supply some control over the direction of sparking. Such directional manipulation can only be accomplished before the catheter is introduced into the patient's body. No means are disclosed for directing the random sparking of the "antenna" once introduced into the desired artery.

An example of an asymmetrically shaped electrode or energy applicator is seen in U.S. Pat. No. 4,311,154 of Sterzer. The Sterzer patent discloses a device to be used in the treatment of a cancerous tumor with high temperatures, or hyperthermia. Sterzer describes a device for hyperthermic treatments utilizing microwave energy so that heat radiates nonsymmetrically from the surface of the instrument. Sterzer does not utilize RF sparking and, like the Rosen patent, does not contemplate the use of means for directing the energy once the device is in place within the body.

The examples discussed above where RF sparking has been used for the resolution of atherosclerotic plaque employ relatively unsophisticated means. The RF spark is a very powerful and intense force to be let loose within the human body. Means for effectively harnessing the vast potential of RF sparking angioplasty have not been disclosed prior to this invention.

SUMMARY OF THE INVENTION.

This invention relates to an improved device for the ablation or resolution of atherosclerotic plaque by use of RF sparking. The present invention adapts the electrosurgical electrode so that it may be incorporated into a catheter that may be manipulated to an arterial site of atherosclerotic plaque. The RF angioplasty catheter of the present invention has a segmented head, so that it is possible to control nonsymmetrical sparking from a plurality of electrodes.

Combined with real time visualization techniques, the device of the present invention allows for greater control and precision when utilizing RF sparking to resolve atherosclerotic plaque. The RF spark is an extremely powerful and concentrated source of heat within the artery. By the use of a segmented catheter head, the somewhat random nature of the sparking may be actively directed towards the section of the artery surface containing the plaque build-up of interest.

Controlling the direction of sparking from the electrode head makes it possible to increase the energy of the RF current utilized. By employing increased energy sparks, the material making up the atherosclerotic plaque may be almost totally disintegrated. The material constituting the plaque may be reduced to such fine particles that removal of residue from the plaque resolution site is not necessary.

It is necessary to optimize the modulation of the RF current delivered to the sparking site. Even though the segmented catheter head greatly increases the specificity of the sparking action, it is still crucial to minimize temperature increases in the tissues surrounding the plaque. The higher energy sparks employed requires that pulsed modulation of the frequency be carefully controlled in order to allow the dissipation of heat to occur between the heat-generating spark pulses.

The catheter device of the present invention may have an elongated flexible hollow body that has a single open cavity capable of delivering fluids to the site of plaque resolution. At the far, or distal end, of the device, there is a plurality of sparking sites or electrodes spaced about the exterior circumference of the generally cylindrical catheter device. The RF energy transmitted to the distal end of the catheter may be selectively applied to any one of the various electrodes. Visualization of the artery will determine which wall or walls of the artery contain the plaque build-up to be resolved and will determine which electrode should be activated.

BRIEF DESCRIPTION OF THE DRAWINGS

FIG. 1 is an isometric view of the distal end of an embodiment of the present invention.

FIG. 2 is a schematic view of a monopolar embodiment of the present invention.

FIG. 3 is a fragmentary axial cross-sectional view of the embodiment of the invention shown in FIG. 1.

FIG. 4 is a distal end view of the device shown in FIG. 3.

FIG. 5 is a radial sectional view of the device shown in FIG. 3 and is taken along the line 5—5 of FIG. 3.

FIG. 6 is another radial sectional view of the device shown in FIG. 3 and is taken along the line 6—6 of FIG. 3.

FIG. 7 is an isometric view of the distal end of an embodiment of the present invention.

FIG. 8 is a distal end view of an embodiment of the invention.

FIG. 9 is a radial sectional view analogous to FIG. 6 of an embodiment of the device.

FIG. 10 is a radial sectional view analogous to FIG. 5.

FIG. 11 is a radial sectional view analogous to FIG. 6.

DESCRIPTION OF THE PREFERRED EMBODIMENT.

FIG. 1 shows the distal end 20 of a atherosclerotic plaque resolving device constructed according to the teachings of the present invention. FIG. 3 shows a cross-sectional view of the entire device, which is generally referred to, in total, as numeral 10. The device 10 is constructed, both by use of the appropriate size and materials, so that it may be inserted within and along the lumen of a blood vessel. Such devices are generally referred to as catheters, and may be manipulated to the desired location in the blood vessel or artery. The desired location is the site of atherosclerotic plaque build-up. Usually, the plaque site is causing reduced blood flow through the vessel or artery.

The device and method of the present invention is particularly suited for the ablation of atherosclerotic plaque located within the arteries leading to the heart. The device and method disclosed herein has, however, significant advantages over the prior art that may be useful in a number of invasive surgical techniques. The device of the present invention may be used, for example, in the following procedures: the ablative treatment of fallopian tubes; the removal of colon obstructions, the removal of blood clots or tissue build-up within the blood vessels of the brain; and the removal of undesirable intestinal tissue. In each of these surgical procedures—and in the other invasive surgical techniques—a catheter is manipulated to the desired location within the body via the lumen of a tubular body member, and energy is applied to the distal end of the catheter in order to ablate or resolve tissue.

Introduction of the device 10 to the appropriate site may be accomplished by use of a guidewire. A guidewire, with the appropriate bends and turns, is "threaded" through an arterial pathway to the desired point of plaque build-up. The device 10 may then be easily passed over the path of the guidewire to the correct arterial site.

The device 10 includes an elongated hollow tubular body 12. The body 12 is usually flexible, and constructed of an electrically insulative material. Any of a number of polymeric or plastic materials may be employed for this purpose. The distal end 20 of the device 10 includes a plurality of electrodes 14. The electrodes 14 each constitute a monopolar electrosurgical electrode. The electrodes 14 may be constructed of any conductive metal or metallic alloy that is capable of retaining its form or shape when exposed to the extremely high temperatures generated by RF sparking. For example, the electrodes 14 may be composed of stainless steel, tungsten, platinum, titanium, zirconium or any of the other so-called refractory metals. Alloys of the refractory metals may also be employed.

The distal end 20 of the device includes a generally flat end surface 22. The interior 16 of the tubular body 12 of the catheter 10 has a generally constant diameter throughout the axial length of the catheter. Each of the electrodes 14 is separated from each other by the insulative material of the tubular body 12, and exists in part on the circumference of the exterior surface of the tubular body 12 adjacent to the end surface 22, and in part planar to the end surface 22. Each electrode 14, therefore, consists of front 15 and radial 17 elements that are of unitary construction. The RF energy selectively delivered to each of the electrodes 14 will create sparking from the electrode 14 to the atherosclerotic plaque.

In a monopolar device of the present invention as is schematically shown in FIG. 2, the return path for the RF current introduced into the body tissue is through a patient plate 92. The patient plate 92 is a relatively large dispersive plate that is attached to the body of the patient in order to establish contact with a significant amount of body surface area. The patient plate is typically placed onto the hip, thigh, buttock or belly of the patient. Conduction from the patient to the return electrode is maximized by applying electroconductive gel to the points of contact.

The device 10 may also be constructed as a "bipolar" RF sparking source. In such an embodiment, a single return electrode may be included among the plurality of electrodes 14 at the distal end of the device 10. The RF sparking would thereby proceed from the selected electrode 14 to the return electrode. In such an embodiment a single return electrode may be a large conductive ring 93 distal to electrodes 14 with a surface area from 5 to 20 times larger than that of any of the delivery electrodes 14. In another bipolar embodiment of the present invention, the power generator output and return may be adapted so that any one of the plurality of electrodes can serve as either the delivery or return electrode. For example, if the electrodes 14 in the device shown in FIG. 1 were numbered A-D and the plaque adjacent electrode A is twice that adjacent to electrodes B and C with the artery nearest electrode D containing no plaque, electrode A would be selected as the return electrode and B and C would be alternated as the delivery or anodic cathode. The plaque adjacent electrode A would receive twice the sparking energy as that adjacent electrodes B and C, and that adjacent electrode D would receive minimal amounts. In this embodiment, the directional specificity of sparking can be further controlled.

The device 10 is attached to and activated by a high-frequency, high voltage power supply 98. There are several such power generators marketed for use in electrosurgery. Typically, the energy is radio-frequency. Each electrode 14 is coupled to the power supply via a wire conductor 40 that runs the entire length of the tubular body 12. Each wire 40 may be electrically insulated.

The proximal end 50 of the catheter 10 has a "Y" shaped portion 52 that has a straight through passage 53 and a branch passage 54. The interior 16 of the tubular body 12 may be accessed from either the straight through 53 or the branch 54 passage. The wire conductors 40 are coupled to the generator, and prior to insertion into the catheter 10 via the branch passage 54 may be bundled together to form a single transmission wire 42, as shown in FIG. 9, or may remain separated.

The RF generator 98 must be adapted via an electrode switching device 96 such that the output of the generator may be selectively applied to one of the wire conductors 40, and therefore to one of the electrodes 14. Further modification of the generator via a device for waveform modulation 95 must be performed in order to create the optimized modulated waveform. The optimal waveform provides a RF pulse of energy strong enough to create a spark that will disintegrate the atherosclerotic plaque with minimum residue formation. At the same time, the waveform must be modulated such that there is not an excess heat build-up in the tissue adjacent to the plaque destruction site. Appropriate time periods in which heat may be dissipated between bursts of energy will enable adequate cooling periods for the adjacent tissues.

It is thought that commonly available electrosurgery generator units may be adapted to provide the proper RF current; for example, a Bovie "Specialist" 75 Watt ES, Electro-Surgery Unit or similar Valleylabs unit. The frequency of the wave form employed will be between 0.05 and 200 megahertz and the voltage will have a magnitude of several hundred volts. To achieve the optimum output modulation, a digital controller 93 will be connected in series with the generator to control pulse width of RF burst, on and off times and number of pulses.

The transmission wire 42 or wire conductors 40 enter the catheter 10 via the branch passage 54 at the proximal end 50 of the catheter 10. In FIG. 9, the embodiment of the invention utilizing a single transmission wire 42, the transmission wire 42, which contains each of the wire conductors 40, is constructed so that each of the wire conductors 40 is electronically insulated from each other. In addition, the exterior surface of the transmission wire 42 is coated with an insulating material. In the preferred embodiment of the invention, each of the wire conductors 40 will be separately insulated, and will proceed separately through the catheter as seen in FIGS. 3, 5 and 6.

FIG. 6 shows a radial sectional view of the catheter 10 at a point between its distal 20 and proximal 50 ends. As is shown, the wire conductors 40 are located within the interior cavity 16 of the tubular body 12. The wire conductors 40 are designed so that they will not take up significant amounts of the interior 16 volume of the tubular body 12 and that the individual wires will not cross talk with each other. Room must be allowed for the passage of fluids to the plaque destruction site or to encompass the guide wire used to properly place the catheter 10.

As can be seen in FIG. 3, the wire conductors 40 run nearly the full length of the tubular body 12. At some point 45 just adjacent the distal end 20 of the catheter 10, the individual wire conductors 40 proceed through the tubular body 12 and are coupled to the electrodes 14. FIG. 5 is a radial sectional view of the catheter 10 at the point 45 where the wire conductors 40 each connect to its corresponding electrode 14.

FIGS. 10 and 11 show an additional embodiment of the invention wherein the wire conductors 40 are separately contained within separate lumens within the tubular body of the cathode 10.

The device 10 of the present invention is used for resolving or ablating atherosclerotic plaque or clots within the interior of vessels or arteries. The method of plaque resolution with such a device requires the use of some means for visualizing the interior of the vessel where plaque destruction is to occur. This can be accomplished by placing ultrasound transducers 85, as shown in FIG. 7 at the catheters distal end or under the electrodes 14. The transducers 85 send and receive ultrasonic signals which are processed using traditional ultrasonic processing means 100 and this displayed on video terminals 102 as shown in FIG. 2. Other visualization techniques would include, but would not be limited to, the following: the introduction of radionuclear dyes that allow for radiographic visualization use of other dyes suitable for introduction at the site of plaque destruction—or in the bloodstream generally—that are detectable by X-ray or other detection techniques, high resolution biplane angiography, and fiber optics introduced along the catheter pathway that provide an actual picture of the interior of the artery or vessel.

Whatever means are used to determine the site of plaque build-up that requires treatment, the initial step is generally the placement of the catheter adjacent to the proposed destruction site. As described above, the appropriate positioning may be accomplished with the aid of a guidewire. Guidewires are constructed so that the wire will be introduced into an artery—either through the leg or arm—and threaded to the desired position. The placement of catheters is a well known and often performed procedure in connection with balloon angioplasty and other invasive surgical procedures. In the present invention the placement is critical not only with respect to the extension of the catheter distal end through an artery, but also with respect to the circumferential orientation of the catheter since the RF energy is applied differentially along the circumference to correspond to differential plaque build-up.

When utilizing a guidewire to help manipulate the distal end 20 of the catheter 10 to the appropriate location, the end of the guidewire exiting the patient may be used to guide the catheter 10 by use of the hollow interior 16 of the tubular body 12. The guide wire can be removed from the interior of the catheter when resolution is to begin, or may be maintained in place if required by the attending physician.

The interior cavity 16 of the catheter 10 may also be used to introduce fluids to the site of plaque destruction. For example, as an aid to visualization it may be desirable to flush the plaque destruction site. The introduction of dyes to aid the visualization process may also be accomplished via the interior cavity 16.

The interior cavity may also be valuable in order to place a fiber optic element at the site of atherosclerotic plaque build-up. This could be accomplished by removal of the guidewire and introduction of the fiber optic—guided through the interior chamber—to the appropriate site.

The electrodes 14 at the tip of the distal end 20 of the tubular body 12 are shaped so that sparking may occur in both forward and radial directions. It is therefore possible to resolve plaque that has built up to such an extent that the catheter 10 is prevented from proceeding further along the arterial pathway. RF sparking from the front portions of the electrodes 14 will allow some forward directed sparking. Generally, the exterior diameter of the tubular body 12 is sized such that it is substantially smaller than the interior diameter of the arteries and vessels it will be encompassed by. Unless the atherosclerotic plaque build-up has progressed extremely far, it should be possible to place the distal end 20 of the catheter 10 in a position so that the plaque to be resolved will be generally planar to the side elements 17 of the electrode 14 selected to ablate the plaque.

Once the distal end 20 of the catheter 10 is properly placed, the operator must determine by consultation with the visualization technique utilized which surfaces of the artery or vessel require ablation. Rather than the random sparking delivered from the RF sparking electrodes of the current devices, it is possible to direct sparking towards those surfaces that require ablation.

In an additional embodiment of the device 10 (shown in FIGS. 7 and 8), the electrodes 14 consist of a plurality of split rings spaced along the exterior surface of the distal end 20 of the catheter. Each of the split rings 80 are separated from each other by a relatively small amount of the insulative material that comprises the bulk of the catheter 10. Each ring 80 is "split" into a plurality of separate electrodes by equally spaced portions of insulative material. In such an embodiment it may be useful to incorporate end electrodes 89 on the relatively flat end of the distal end 20 of the catheter 10 as seen in FIG. 8. It would be possible to include a narrowed opening into the interior of the catheter to allow the expulsion of dyes or an interior catheter, as shown, or to "cap" the hollow catheter 10.

The embodiment of the invention shown in FIGS. 7 and 8, as can the embodiment shown in FIG. 1, may be adapted to serve as either monopolar or bipolar electrosurgical catheters. The embodiment shown in FIG. 7 has a total of 12 electrodes. When adapted to perform as a bipolar device in which each of the 12 electrodes may be selected to function as the anode or the cathode, the locational specificity for sparking at the site of plaque build-up is greatly enhanced. In such an embodiment, in addition to means for optimally modulating the wave form of the current flowing from the generator, the electrode switching means 96 must be adapted to select which of the electrodes will serve as the anode and which will serve as the cathode or return path.

I claim:

1. An electrosurgical device for resolving an occlusive deposit in a lumen of a blood vessel having a distal end which is insertable within and along the lumen of the vessel and manipulatable therethrough to a desired position where the device is operated to resolve the occlusive deposit by radio frequency sparking, said device comprising:

(a) an elongated flexible hollow tube having a distal end, a proximal end, and a diameter smaller than the diameter of the vessel lumen into which said device is being inserted;

(b) a plurality of electrodes proximate said distal end of the tube, the electrodes being spaced radially about the tube;

(c) selection means in electrical communication with the electrodes for selectively supplying a radio frequency electrical current to at least one of said electrodes whereby said at least one electrode becomes a transmitting electrode and a user can limit the radial direction of radio frequency sparking to the radial location of the occlusive deposit corresponding to the transmitting electrode so as to minimize damage to the vessel; and current return means on the tube for returning current to the selection means.

2. The device of claim 1 wherein at least one of said electrodes serves as the current return means and said radio frequency sparking occurs between said transmitting electrode and said return electrode.

3. The device of claim 2 wherein the selection means further comprises means for selecting which of said electrodes will serve as said return electrode.

4. The device of claim 2 wherein said distal end further includes a tip, and said electrodes further include electrodes on the tip of said distal end.

5. The device of claim 2 further comprising modulation means for modulating the wave form of said radio frequency electrical current so that said sparking will resolve said occlusive deposit while minimizing heat build-up in tissue adjacent to said occlusive deposit.

6. The device of claim 2 wherein said radio frequency electrical current includes a frequency, a voltage and a current, and further comprising means for adjusting the frequency, voltage and current of the radio frequency electrical current so that said sparking will resolve said occlusive deposit while minimizing heat buildup in tissue adjacent said occlusive deposit.

7. The device of claim 2 wherein said electrodes are composed of a refractory metal selected from the group consisting of stainless steel, tungsten, platinum, zirconium and titanium.

8. The device of claim 2 wherein said tube is an electrically insulative material.

9. The device of claim 2 wherein said electrodes are electrically associated with said selection means via individual wires carried within said hollow tube.

10. The device of claim 2 further comprising ultrasound transducers on said hollow tube adjacent to said electrodes at said distal end.

11. The device of claim 2 wherein said electrodes consist of a plurality of split rings adjacent said distal end.

12. The device of claim 11 wherein said electrodes are electrically insulated from one another.

13. The device of claim 2 further comprising means for supplying or removing fluids from a site of-tissue resolution and wherein said proximal end has a "Y" shaped portion consisting of a straight through passage and a branch passage, said straight through passage being associated with said means for supplying or removing fluids from the site of tissue resolution.

14. The device of claim 1 further comprising means for visualizing the interior surfaces of said desired position within said vessel.

15. The device of claim 14 wherein said means for visualizing the interior surfaces of said desired position within said vessel employ ultrasound information.

16. The device of claim 1 wherein the current return means comprises a conductive ring disposed around the circumference of the tube proximate the plurality of electrodes.

17. A method for reducing the flow restriction effects of an occlusive deposit located at a point in a vessel, comprising:

(a) obtaining access to the interior of said vessel;

(b) inserting the distal end of a catheter consisting of an electrical conductor terminated in a plurality of radially spaced electrodes into said vessel;

(c) adjusting the position of said electrodes adjacent to said point;

(d) identifying the radially spaced electrodes adjacent to the occlusive deposit; and (e) selectively applying radio frequency energy to the identified electrodes adjacent said occlusive deposit so that said energy will cause sparking from only the identified electrodes to resolve the occlusive deposit while minimizing damage to the vessel.

18. The method described in claim 17 wherein one of said electrodes serves as a return electrode and at least one of said electrodes serves as a transmitting electrode and said sparking occurs between said transmitting electrode and said return electrode.

* * * * *